United States Patent [19]

Russell

[11] Patent Number: 4,831,147

[45] Date of Patent: May 16, 1989

[54] RESOLUTION OF ENANTIOMERS OF HERBICIDAL 2-(4-ARYLOXYPHENOXY) PROPIONATES BY CHIRAL TWO-PHASE EXTRACTION

[75] Inventor: John W. Russell, Midland, Mich.

[73] Assignee: The Dow Chemical Company, Midland, Mich.

[21] Appl. No.: 215,463

[22] Filed: Jul. 5, 1988

[51] Int. Cl.$^4$ .................................. C07B 57/00
[52] U.S. Cl. ............................ 346/302; 71/109; 562/401; 562/470; 562/471
[58] Field of Search ............... 562/401, 470, 471; 546/302

[56] References Cited

U.S. PATENT DOCUMENTS 4,531,969 7/1985 Nestler et al. ................ 71/108
4,766,220 8/1988 Gras ............................ 546/302

FOREIGN PATENT DOCUMENTS

WO87/00165 1/1987 PCT Int'l Appl. .

OTHER PUBLICATIONS

Pettersson et al, *Journal of Chromatography*, vol. 282, pp. 671–684, 1983.
Pettersson, *Journal of Chromatography*, vol. 316, pp. 553–567, 1984.

Primary Examiner—Werren B. Lone
Assistant Examiner—Vera C. Clarke
Attorney, Agent, or Firm—Craig E. Mixan; Ronald G. Brookens

[57] ABSTRACT

Racemic mixtures of 2-(4-aryloxyphenoxy)propionic acids are resolved into their optically active enantiomers by dissolving the racemate with at least one equivalent of a cinchona alkaloid in a halogenated hydrocarbon solvent and by extracting with a polyhydroxylic solvent.

13 Claims, No Drawings

RESOLUTION OF ENANTIOMERS OF HERBICIDAL 2-(4-ARYLOXYPHENOXY) PROPIONATES BY CHIRAL TWO-PHASE EXTRACTION

FIELD OF THE INVENTION

This invention relates to a method for the chiral resolution of racemic mixtures by a two-phase extraction system. More specifically, this invention relates to the extractive resolution of racemic mixtures of 2-(4-aryloxyphenoxy)propionic acid herbicides.

BACKGROUND OF THE INVENTION

The herbicidal activity of 2-(4-aryloxyphenoxy)propionic acids and derivatives thereof is well known in the art. Furthermore, optical isomers are often known to exhibit enhanced herbicidal activity over the corresponding racemates. For example, U.S. Pat. No. 4,531,969 discloses that the R-enantiomers of certain 2-(4-aryloxyphenoxy)propionic acids and certain derivatives thereof are distinguished by a considerably enhanced herbicidal action compared to the racemic modifications. Since reduced quantities of herbicide are sufficient to achieve comparable levels of control, the application of mixtures enriched in the more efficacious R-enantiomer offers both economical and environmental advantages.

To exploit the agronomic benefits of these advantages, it is necessary to efficiently resolve racemic mixtures of herbicides that are normally produced industrially. Various methods for obtaining high concentrations of individual enantiomers are known. The most common method of resolution of a racemic modification involves its conversion by an optically active reagent into a mixture of diastereomers which can then be separated on the basis of their different physical properties. Diastereomers are generally separated by fractional crystallization, though occasionally by fractional distillation or by chromatography. Once the diastereomers have been separated, they can be reconverted to the individual enantiomers and the optically active resolving agent can be recovered.

Although the physical separation of diastereomers by crystallization, distillation and chromatography are, for example, well documented, separations based on extraction are relatively unknown.

SUMMARY OF THE INVENTION

The present invention provides a method for resolving a racemic mixture of optically active enantiomers of a 2-(4-aryloxyphenoxy)propionic acid of formula (I)

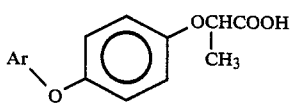

wherein
Ar is an unsubstituted or a substituted phenyl or pyridinyl ring
which comprises dissolving the racemate and a cinchona alkaloid in a halogenated hydrocarbon solvent and extracting with a polyhydroxylic solvent.

As used herein, the following terms have the following meanings. The terms "halo" and "halogen" refer to F, Cl, Br and I. By "cinchona alkaloid" is meant one of the four alkaloids isolated from cinchona bark, namely cinchonine, cinchonidine, quinine and quinidine. By "halogenated hydrocarbon solvent" is meant any halogenated aliphatic hydrocarbon of 1 to 3 carbon atoms inclusive or admixtures thereof. The term "polyhydroxylic solvent" refers to an organic solvent which has at least two hydroxyl groups, and which is at least partially immiscible with the halogenated hydrocarbon solvent.

DETAILED DESCRIPTION OF THE INVENTION

With the development of the R-enantiomers of various 2-(4-aryloxyphenoxy)propionic acid derivatives as herbicides, the resolution of enantiomers has assumed much greater commercial significance. Although extraction is generally a much simpler and straight-forward unit operation in comparison to fractional crystallization or sorbent separation, for example, the difficulty of enantiomer resolution is so extreme that extraction has only recently been considered a viable possibility.

The present invention provides a method for resolving a racemic mixture of optically active enantiomers of a 2-(4-aryloxyphenoxy)propionic acid of formula (I)

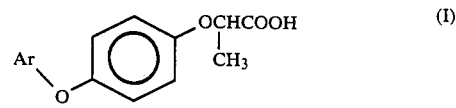

wherein
Ar is an unsubstituted or a substituted phenyl or pyridinyl ring
which comprises dissolving the racemate and a cinchona alkaloid in a halogenated hydrocarbon solvent and extracting with a polyhydroxylic solvent.

The 2-(4-aryloxyphenoxy)propionic acids to which the present method may be applied are disclosed, for example, in U.S. Pat. Nos. 4,046,553; 4,332,960; 4,332,961; 4,531,969; 4,550,192 and 4,565,568 and in European patent application publication Nos. 0,000,483; 0,001,473 and 0,003,890.

Particularly valuable examples of 2-(4-aryloxyphenoxy)propionic acids to which the present method may be applied are of formula:

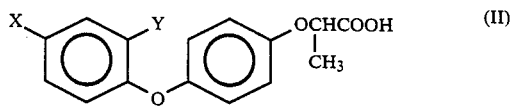

wherein
X is $CF_3$ or halogen, and
Y is hydrogen or halogen, and

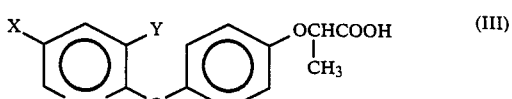

wherein X and Y are as previously defined.

Of the four alkaloids isolated from cinchona bark, quinine and cinchonidine are most often used for the formation of diastereomers with acids. The use of quinine is most preferred in the present method.

Of the halogenated hydrocarbon solvents used in the present invention, those in which all or most of the hydrogens have been replaced by halogens are preferred. These solvents include, but are not limited to, carbon tetrachloride, perchloroethylene, trichloroethylene, 1,1,2-trifluoro-1,2,2-trichloroethane, chloroform and admixtures thereof.

The preferred polyhydroxylic solvents of the present invention have the hydroxyl groups adjacent to one another. Examples of such preferred polyhydroxylic solvents include, but are not limited to, alkylene glycols of 2 to 4 carbon atoms inclusive.

The extractive resolution is typically performed by dissolving the cinchona alkaloid and the racemic 2-(4-aryloxyphenoxy)propionic acid into the halogenated hydrocarbon solvent and extracting with the polyhydroxylic solvent.

The ratio of cinchona alkaloid to (aryloxyphenoxy)propionic acid can range from 0.5/1 to greater than 5/1. In general, the higher the ratio of alkaloid to acid, the greater the discrimination between the enantiomers in the product phase, i.e., the R/S ratio. Beyond a certain ratio, little if any enhanced resolution is achieved. Alkaloid to acid ratios in the range of about 0.8 to about 1.5 are preferred.

By "product phase" is meant that phase which contains a more enhanced ratio of the desired isomer. Whether the R- or S-enantiomer is found in a particular phase, e.g., the halogenated hydrocarbon phase, is determined by the choice of alkaloid and the particular 2-(4-aryloxyphenoxy)propionic acid employed. Increased concentrations of both the alkaloid and the propionic acid solutes promote higher recoveries per pass, but with a drop-off in enantiomer resolution. Concentrations of the alkaloid and the propionic acid can range from parts per million to up to several percent.

Different ratios of solvents also affect the yield in the product phase and the enantiomer resolution. Changing the solvent ratio generally improves one while diminishing the other; thus a compromise is necessary. The concentrations of solutes also affect optimum solvent ratios which can range from 95/5 to 5/95. Near-optimal operating conditions can readily be determined by a few range-finding experiments altering the parameters discussed above.

A single pass extraction typically changes the enantiomer ratio in the product phase from 50/50 of the racemate to a preponderance of one enantiomer of from about 51/49 to about 2/1. By using a multistage extraction process, (aryloxyphenoxy)propionic acids of desired optical purity can be produced.

The cinchona alkaloid can be recovered from the extract by pH-controlled precipitation or extraction. The product, enriched in the desired enantiomer, is isolated from the product phase by conventional techniques. The by-product, enriched in the undesired enantiomer, is similarly isolated from the other phase and can be racemized by conventional procedures for recycle in the extraction process.

The following examples illustrate the invention and are not to be construed as a limitation thereon.

EXAMPLE 1

A mixture of 0.1 gram (g) of quinine (6 mole percent excess) and 0.1 g of racemic 2-(4-((3-fluoro-5-trifluoromethyl-2-pyridinyl)oxy)phenoxy)propionic acid was dissolved in 85 milliliters (mL) of carbon tetrachloride and the solution was extracted for 1 minute (min) with 15 mL of ethylene glycol (EG). The carbon tetrachloride phase was analyzed for enantiomer ratio and was found to contain 60R/40S.

EXAMPLE 2

A series of extraction experiments were performed in which the solvents were measured by volume to a total of 100 mL and were placed into an 8 ounce (oz) bottle containing quinine and racemic 2-(4-((3-fluoro-5-trifluoromethyl-2-pyridinyl)oxy)phenoxypropionic acid. The contents were shaken for 1 min and after phase separation the halogenated hydrocarbon phase was analyzed for enantiomeric content. The percent of the R-enantiomer found in the halogenated phase versus the amount of R-enantiomer initially added was calculated by comparison with a standard and by measurement of the volume of halogenated hydrocarbon phase collected after the extraction. The results are summarized in Table I.

TABLE I

Enantiomer Ratios From Extraction of Racemic 2-(4-((3-Fluoro-5-trifluoromethyl-2-pyridinyl)oxy)phenoxy)propionic Acid $$CF_3\text{-pyridinyl-F-O-phenyl-OCHCOOH with } CH_3$$

| Experiment | Solvents (mL) | Quinine (g) | (g) | R/S (Halogenated Phase) | % of R in Halogenated Phase |
|---|---|---|---|---|---|
| 1 | 15Ethylene Glycol/85CCl₄ | 0.1 | 0.1 | 59/41 | — |
| 2 | 50EG/50CCl₄ | 0.1 | 0.1 | 60/40 | — |
| 3 | 15EG/85CCl₄ | 0.2 | 0.1 | 59/41 | — |
| 4 | 15EG/85CCl₄ | 0.1 | 0.1 | 60/40 | 17 |
| 5 | 15EG/85CCl₄ | 0.0755 | 0.1 | 56.1/43.9 | 26.5 |
| 6 | 15EG/85CCl₄ | 0.0472 | 0.1 | 52.7/47.3 | 30.2 |
| 7 | 15EG/85CCl₄ → reextract EG 15EG/85CCl₄ | 0.1 | 0.1 | 58/42 / 59/41 | 23 / 16 |
|  | reextract CCl₄ 15EG/85CCl₄ |  |  | 69/31 | 2.4 |
| 8 | 15EG/85CCl₄ | 0.3 | 0.3 | 58/42 | 32 |
| 9 | 15EG/85CCl₄ | 0.5 | 0.5 | 56/44 | 37 |

TABLE I-continued
Enantiomer Ratios From Extraction of Racemic 2-(4-((3-Fluoro-5-trifluoromethyl-2-pyridinyl)oxy)phenoxy)propionic Acid

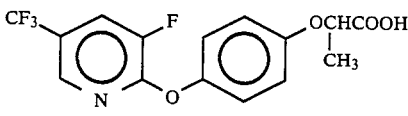

| Experiment | Solvents (mL) | Quinine (g) | (g) | R/S (Halogenated Phase) | % of R in Halogenated Phase |
|---|---|---|---|---|---|
| 10 | 25EG/75CCl₄ | 0.5 | 0.5 | 58.42 | 22 |

EXAMPLE 3

A series of extraction experiments were performed in which quinine and a racemic (aryloxyphenoxy)propionic acid were extracted for 1 min with a 100 mL total of two phases as listed in Table II. The quantity of quinine was held constant at 0.1 g and the weight of the (aryloxyphenoxy)propionic acid was adjusted to maintain a 6 mole percent excess of quinine. The halogenated hydrocarbon phase was analyzed for enantiomeric content. The percent of the R-enantiomer found in the halogenated phase versus the amount of R-enantiomer initially added was calculated by comparison with a standard and by measurement of the volume of the halogenated hydrocarbon phase collected after the extraction. The results are summarized in Table II.

TABLE II
Enantiomer Ratios From Extraction of Racemic 2-(4-Aryloxyphenoxy)propionic Acid

| Compound | Extraction Solvents | R/S (Halogenated Phase) | % of R in Halogenated Phase |
|---|---|---|---|
| CF₃–pyridinyl(F)–O–C₆H₄–OCH(CH₃)CO₂H | 15EG/85CCl₄ | 60.4/39.6 | 20.3 |
| CF₃–pyridinyl(Cl)–O–C₆H₄–OCH(CH₃)CO₂H | 15EG/85CCl₄ | 60.1/39.9 | 29.1 |
| CF₃–pyridinyl–O–C₆H₄–OCH(CH₃)CO₂H | (a) 15EG/85CCl₄<br>(b) 15EG/85CCl₄<br>(c) 15EG/20 CHCl₃ + 65CCl₂FCClF₂ | 67.5/32.5<br>67.4/32.6<br>67.0/33.0 | 17.8<br>17.4<br>22.0 |
| Br–C₆H₃(F)–O–C₆H₄–OCH(CH₃)CO₂H | (a) 15EG/85CCl₄<br>(b) 15EG/85CCl₄<br>(c) 15EG/20CHCl₃ 65CCl₂FCClF₂ | 45.8/54.2<br>46.0/54.0<br>46.2/53.8 | 10.7*<br>11.2*<br>7.1* |

*percent of total S instead of R

Various modifications may be made in the present invention without departing from the spirit or scope thereof, and it is understood that I limit myself only as defined in the appended claims.

What is claimed is:

1. A process for resolving a racemic mixture of optically active enantiomers of a 2-(4-aryloxyphenoxy)propionic acid of formula (I)

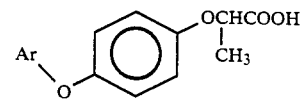

wherein
Ar is an unsubstituted or a substituted phenyl or pyridinyl ring
which comprises dissolving the racemate and a cinchona alkaloid in a halogenated hydrocarbon solvent and extracting with a polyhydroxylic solvent.

2. The process of claim 1 in which Ar is

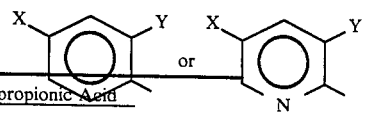

wherein
X is CF₃ or halogen and
Y is hydrogen or halogen.

3. The process of claim 1 in which the ratio of cinchona alkaloid to 2-(4-aryloxyphenoxy)propionic acid is from about 0.8 to about 1.5.

4. The process of claim 1 in which the cinchona alkaloid is quinine.

5. The process of claim 1 in which the halogenated hydrocarbon solvent is selected from the group consisting of carbon tetrachloride, perchloroethylene, trichloroethylene, 1,1,2-trifluoro-1,2,2-trichloroethane, chloroform and admixtures thereof.

6. The process of claim 1 in which the polyhydroxylic solvent is an alkylene glycol of 2 to 4 carbon atoms inclusive.

7. The process of claim 2 in which the ratio of cinchona alkaloid to 2-(4-aryloxyphenoxy)propionic acid is from about 0.8 to about 1.5.

8. The process of claim 2 in which the cinchona alkaloid is quinine.

9. The process of claim 2 in which the halogenated hydrocarbon solvent is selected from the group consisting of carbon tetrachloride, perchloroethylene, trichloroethylene, 1,1,2-trifluoro-1,2,2-trichloroethane, chloroform and admixtures thereof.

10. The process of claim 2 in which the polyhydroxylic solvent is an alkylene glycol of 2 to 4 carbon atoms inclusive.

11. The process of claim 7 in which the cinchona alkaloid is quinine.

12. The process of claim 11 in which the halogenated hydrocarbon is selected from the group consisting of carbon tetrachloride, perchloroethylene, trichloroethylene, 1,1,2-trifluoro-1,2,2-trichloroethane, chloroform and admixtures thereof.

13. The process of claim 11 in which the polyhydroxylic solvent is an alkylene glycol of 2 to 4 carbon atoms inclusive.

* * * * *